United States Patent [19]

Ciorbaru nee Sfartz et al.

[11] 4,201,768

[45] May 6, 1980

[54] PROCESS FOR OBTAINING AGENTS HAVING MITOGENIC AND/OR ADJUVANT PROPERTIES FROM NOCARDIA CELLS AND COMPOSITIONS CONTAINING SUCH AGENTS

[75] Inventors: Rita Ciorbaru nee Sfartz, Fontenay-aux-Roses; Constantin Bona; Louis Chedid, both of Paris; Edgar Lederer, Sceaux; Jean-Francois Petit, Paris, all of France

[73] Assignee: Agence Nationale de Valorisation de la Recherche (ANVAR), Neuilly-sur-Sein, France

[21] Appl. No.: 782,193

[22] Filed: Mar. 28, 1977

[30] Foreign Application Priority Data

Mar. 26, 1976 [FR] France .................................. 76 08972

[51] Int. Cl.² ...................... A61K 39/02; A61K 35/74
[52] U.S. Cl. ........................................ 424/92; 424/195
[58] Field of Search ................................... 424/92, 195

[56] References Cited

PUBLICATIONS

Constantin et al.,–Chem. Abst., vol. 81, (1974), p. 45982k.
Adam et al.,–Chem. Abst., vol. 79, (1973), p. 30388f.
Petit et al.,–Chem. Abst., vol. 79, (1973), p. 64476y.
Adam et al.,–Chem. Abst., vol. 85, (1976), p. 121690p.
Ciorbaru et al.–Chem. Abst., vol. 84, (1976), p. 41997h.
Bona et al.,–Chem. Abst., vol. 82, (1975), p. 123134x.
Azuma et al.–Chem. Abst, vol. 80, (1974), 124749x.
Azuma et al.–Chem. Abst., vol. 83, (1975), p. 6891b.

*Primary Examiner*—Sam Rosen
*Attorney, Agent, or Firm*—Weiser, Stapler & Spivak

[57] ABSTRACT

The invention relates to a process for obtaining agents having mitogenic and/or adjuvant properties, from Nocardia cells.

According to this process Nocardia whole cells are subjected to a rupturing treatment of their walls within an aqueous medium, particularly distilled water. After the separation of the non-ruptured cells and of the wall fragments of the ruptured cells, mitogenic agents are extracted from the remaining aqueous phase. The fractions obtained are useful as laboratory reagents and for the production of medicamentous compositions in which they are associated with a pharmaceutical vehicle.

36 Claims, No Drawings

PROCESS FOR OBTAINING AGENTS HAVING MITOGENIC AND/OR ADJUVANT PROPERTIES FROM NOCARDIA CELLS AND COMPOSITIONS CONTAINING SUCH AGENTS

A related patent application of this application is Ser. No. 571,384, filed Apr. 24, 1974, now issued into U.S. Pat. No. 4,042,678.

The invention relates to agents having non specific mitogenic and or immunostimulant properties. These properties make of them biological reagents of great value for research and diagnosis. These agents, when they are administered to men or animals, can induce a non-specific stimulation of lymphocytes B which is shown by an increased production of antibodies directed against large categories of antigens. Further, they encourage the development of the stem cells, so that their use may be considered in the curative treatment of diseases resulting from deficiencies of immunocompetent and hematopoetic cells.

Fractions having such mitogenic properties have already been obtained from whole cells obtained from Nocardia cultures. They have especially been made the subject of the above-referred to patent application in the name of the applicants, in which a process for obtaining such mitogenic fractions is also described.

These fractions were obtained in particular from a first aqueous fraction, itself separated from a suspension containing the products of digestion of previously delipidated Nocardia cells, in the presence of a muramidase, more particularly of lysozyme, in an aqueous buffered solution. Fractions were obtained which are still more enriched in mitogenic agent, especially by separation of the peptidoglycan fractions dissolved in the first aqueous fraction, and resulting from the fragmentation of the glycan chains of the peptidoglycan, owing to the at least partial hydrolysis of the 1,4-$\beta$ linkages between the alternate N-acetylglucosaminyl and N-acylmuramyl groups in its glycan chains. These fragments of peptidoglycan, of which the valuable non-specific adjuvant and/or immunostimulant properties have been described in another connection, are however revealed as only having a weak or even no mitogenic activity.

The last separation mentioned was effected by filtration on a molecular sieve, for example on gels of the type of those known commercially by the name SEPAHADEX, or according to an alternative of the process, by suspension of a lyophilizate of the aforesaid first fraction in concentrated acetic acid and by recovery, especially by centrifuging, of the undissolved fraction, which contained the mitogenic activity, while the liquid phase retained the adjuvant but not mitogenic peptidoglycan fragments in the dissolved state.

It will also be recalled that the mitogenic fractions extracted from Nocardia cells, according to the process disclosed in the above identified application, also possess adjuvant properties. Such was the case of the fractions obtained after the separation of the peptidoglycan fragments contained within the aqueous medium obtained from the suspension of the cells after digestion of the latter in the presence of lysozyme.

The object of the present invention is to provide a new and more simple process for obtaining mitogenic and/or adjuvant fractions from the same cells. It also relates to the fractions themselves and to compositions formed with said fractions.

Accordingly, the process according to the invention, which is applicable to Nocardia cells, comprises subjecting the whole Nocardia cells to a rupturing treatment within an aqueous medium, particularly within distilled water, separating the non-ruptured cells as well as the wall fragments of the ruptured cells, such as by centrifugation, and recovering the aqueous phase substantially free of cell wall constituents but containing constituents of the cell cytoplasm, which aqueous phase contains fractions having both mitogenic and adjuvant properties.

It has futher been found that it was possible to obtain further enriched fractions having mitogenic and/or adjuvant properties from the liquid phase so obtained.

A further improvement of the process according to the invention thus comprises separating the cytoplasmic membranes or fragments thereof from the liquid phase and recovering the aqueous phase containing the mitogenic and adjuvant activities. Said separation can be achieved, such as by centrifugation under a sufficient acceleration, for instance of the order of 48,000 g, whereby a centrifugation sediment is obtained which contains the cytoplasmic membrane fragments and the ribosomes of the Nocardiae.

Upon further ultra-centrifugation at much higher accelerations, such as at 100,000 g, of the liquid fractions obtained as hereabove, a sediment is obtained which has adjuvant and mitogenic activities. The supernatant which is then essentially formed of cytosols, however does also possess adjuvant and mitogenic properties.

Advantageously, the said ultra-centrifugation is preceeded by a treatment of the preceeding liquid phase with a low amount of magnesium chloride for the sake of aggregating together the residual ribosomes which it may still contain.

The mitogenic fractions obtained at the end of each of the above process steps are, like the mitogenic adjuvants disclosed in the above identified application, active with respect to lymphocytes, particularly the B lymphocytes of several animal species, whereby the non-specific character of the mitogenic properties of the fractions obtained is established. Accordingly, these fractions have properties which are useful for the production of compositions having mitogenic and/or adjuvant properties and, when associated with pharmaceutical acceptable vehicles, provide compositions having properties useful in therapy.

The invention provides new mitogenic agents, notably hydrosoluble ones, quite distinct from the first, in that they are precisely directly derived from the peptidoglycanes of the bacterial walls, whether they come from Nocardiae or other bacterial species. They have a mitogenic activity in vitro and in vivo as well. In the latter case the mitogenic activity shows up not only in mice, but also in other species of animals. They are therefore suitable for the manufacture of administrable compositions in order to put into practice their mitogenic activities.

Other characteristics of the invention will appear in the course of the description of examples of mitogenic agents containing glycan chains and their processes of manufacture.

First of all the conditions in which the walls of the different bacteria may be obtained will be described. The conditions under which the mitogenic agents have been obtained from said walls will be subsequently described.

(a) Culture of *Nocardia rubra*, ATCC 14,898 and *Nocardia opaca*, ATCC 21,953 (strains from the Pasteur Institute of Paris).

The strains indicated above were cultivated in a fermenter of 20 liters, on 14 liters of a medium inoculated with 500 ml of a preculture effected on the same medium.

The medium used for the culture of *Nocardia rubra* was composed of 2.5% of "Heart Infusion Broth" (Difco), 10 ml/liter of glycerol and 0.25 g/liter of $Na_2HPO_4$, 12 $H_2O$, the pH having been adjusted to 7.4–7.6.

The culture medium of *Nocardia opaca* was composed of 0.2% of yeast extract (Difco), 0.4% of meat extract (Difco), 2% of bactopeptone (Difco) and 0.5% of NaCl, the pH having been adjusted to 7.2.

In both cases the cultures were carried out under the same conditions, except with respect to the temperatures of culture (25° C. for *N. rubra* and 30° C. for *N. opaca*). They were carried out under stirring, by rotation of the propeller of the fermenter at 250 revolutions per minute, and with aeration of the medium, at the rate of 2 liters of air per minute.

The cultures were interrupted at the end of 3 to 4 hours. In the case of *N. rubra*, the culture then had a brick red colour.

The cultures were then collected by centrifuging, washed with distilled water and stored at −20° C. until their use.

In order to obtain the walls of these cells, the latter were suspended in five times their weight of distilled water in the container of a homogeniser or "mixer" and subjected to three passages through a pressure grinder known by the trademark MANTON-GAULIN, under a pressure of 750 kg per square centimeter. DNase was added after the first passage.

The homogenised product finally obtained was diluted with three times its volume of distilled water and centrifuged three times for 15 minutes, at 800 g in a cooled centrifuge, the deposits obtained at the end of each of these operations, and containing the unbroken cells, being then eliminated. The liquid phase finally obtained was then subjected to a centrifuging at 27,500 g for 50 minutes. The sediment which contained the crude walls of the treated cells were discarded and the aqueous phase containing the cytoplasmic constituents of the treated cells was recovered.

This phase presented already itself mitogenic and adjuvant properties. A treatment of acid hydrolysis of this aqueous phase with 6 N hydrochloric acid at 110° C. for 18 hours did not result into the freeing in the medium of meso-$\alpha$-$\epsilon$-diaminopimelic acid detectable by analysis of the amino-acids and by thin-layer chromatography. Accordingly, the liquid phase did not appear to comprise contaminants formed by cellular walls, consequently by constituents of its peptidoglycan.

The "crude cytoplasmic fraction" obtained by lyophiliophilisation of this liquid phase was then resuspended in distilled water. The solution obtained was centrifuged at 48,000 g for one hour, whereby a centrifugation sediment containing fragments of the cytoplasmic membranes and ribosome was obtained. This sediment which was separated from the aqueous supernantant was designated and referred to hereafter by "Cy I".

Magnesium chloride was then added to the supernatant to obtain a concentration of $10^{-2}$ M of this salt. It favoured the aggregation of those of the ribosomes which were still contained in this supernatant and their subsequent separation during the centrifugation which followed at 105,000 g for one hour. A new small sediment was obtained which contained a few ribosomes and which is designated hereafter by "Cy II". The supernatant "Cy III" contained the non-centrifugeable cytosols.

It is the "crude cytoplasmic fraction" and the fraction "Cy I" which exhibited the most important mitogenic activities, both on mouse and on rabbit, as shown by the pharmacological tests, the results of which are disclosed hereafter.

PHARMACOLOGICAL PROPERTIES OF THE FRACTIONS OBTAINED

The mitogenic agents according to the invention possess among others the capacity of stimulating in a nonspecific way the B lymphocytes cells derived from the bone marrow. This activity was demonstrated by the aptitude of splenic lymphocytes (from mouse and rabbit) to absorb (by incorporation) more tritium-containing thymidine than the B lymphocyte cells of the controls.

(1) Culture of the lymphocytes

Lymphocytes were separated from the spleens of mice or rabbits, by having recourse to the technique of C. BONA et al, Eur. J. Imm., 2, 434, 1972. Various types of mice have been used, notably from 2 to 3 months old AKR mice and from four to eight weeks old mice, of the athymic NUDE mouse species, reared at the C.N.R.S. laboratory of Orleans, belonging to a wild non-inbred progeny for nu mutation, and coming from "The Institute of Animal Genetics" of Edinburgh.

Recourse has also been had to splenic cells of from four to six weeks old BOUSCAT rabbits, coming from the breeding of the PASTEUR INSTITUTE of Garches.

$1.5 \times 10^6$ splenic lymphocytes of mice were cultivated for 48 hours, at 37° C., in 1 ml of the medium known as the RPMI-1640 (Eurobio), to which 5% of foetal calf serum (Flow-labs) had been added.

In the same way $2.5 \times 10^6$ splenic lymphocytes of the rabbit were cultivated for 72 hours, at 37° C., in 1 ml of the medium known as the "Eagle medium", to which had been added 10% of autologous serum inactivated by heating for 30 minutes at 56° C.

(2) Incorporation of tritium-containing thymidine

1 $\mu$Ci. of $^3$H-thymidine (1Ci/mMole, Saclay, France) was added to each culture 16 hours before the cells were harvested. At the end of the incubation, an amount 100 times greater of non-radioactive thymidine was added. After centrifuging at 450 g for 10 minutes, the supernatant was removed, the deposit was precipitated with trichloracetic acid and resuspended according to the conventional techniques, before being measured on the scintillation counter.

As may be found by examination of Table I which follows, the agents according to the invention which have been tested have all a mitogenic action which shows itself by the increase of the incorporation of tritium-containing thymidine by the splenic lymphocytes of the animals studied. In the left-hand columns the various fractions are identified. There has been indicated in the columns corresponding to the animals which provided the lymphocytes tested, the observed values of the stimulation index of the agents tested, at the doses indicated between brackets at the side of the corresponding values of the index of stimulation. It is recalled that the stimulation index is the ratio of the radio-activity of the stimulated cells to those of control cells.

(c) Evaluation of the granuloma at the level of the injection site.

TABLE I

| Nature of the product | Mitogenicity (index of stimulation) | | |
|---|---|---|---|
| | AKR mice | NUDE mice | Rabbit |
| "Crude cytoplasmic fraction" of N.rubra (lyophilisate) | 6.64 (100 µg) | 9.95 (100 µg) | 4.28 (100 µg) |
| Cy I of N. rubra | 9.26 (100 µg) | — | 8.29 (100 µg) |
| Cy II of N. rubra | 9.75 (100 µg) | — | 6.85 (100 µg) |
| Cy III of N. rubra | 8.56 (100 µg) | — | 1.57 (10 µg) |
| Cy I of N. opaca | 2.01 (1 µg) | 9.53 (10 µg) | 2.84 (100 µg) |

As may be found, in practically all cases an increase of the measured stimulation index was observed. The agents derived from cells of N. rubra are particularly active. Such was also the case of the "crude cytoplasmic fraction" of N. ruba and of the "Cy I" fraction of N. rubra at doses of 100 µg respectively in mouse and on rabbit. Similar results have been obtained with the "Cy I" fraction of N. rubra with respect to lymphocytes originating from human circulating blood. These results clearly establish the non-specific character of the mitogenic agents according to the invention. Let it be pointed out also that the mitogenic activities observed in the NUDE mice established that agents according to the invention are active on B lymphocytes.

(3) Adjuvant properties

Female Hartley guinea pigs weighing 300–350 g were injected in the pad of each rear paw with a water-in-oil emulsion containing equal parts of a solution of ovalbumin (50 mg/ml of isotonic solution) and either a Freund complete adjuvant (FCA) or a Freund incomplete adjuvant (FIA) containing (with the exception of the control preparation) the fractions studied at the dosages mentioned in Table II hereinafter.

The adjuvant activity was estimated under the following conditions:

(a) Determination in samples of serum taken 21 days after the injection, of the antibody titre expressed in µg/ml of serum of the antigen-antibody precipitate at the equivalence point;

(b) Measurement of the delayed hypersensitivity to ovalbumin (dosages of 10 and 100 µg) in other animals, by cutaneous reaction 4 weeks after the injection, this is expressed by the diameter in mm of the erythema (E), hardening (I) and necrosis (N) 48 hours after the injection of ovalbumin.

As can be seen from Table II hereafter, all the studied fractions possess significant adjuvant properties, at least as high as that of the control which had received a Freund's complete adjuvant (FCA).

TABLE II

| Tested fractions | Dosis (µg/aminlas) | Rate of antitumoral antibodies (µg/ml) | | Granuloma at the injection site | delayed sensitivity to the doses of ovalbumine | |
|---|---|---|---|---|---|---|
| | | Number of animals | Medium ± mean error | | 10 µg | 100 µg |
| Freund's incomplete adjuvant (FIA) | 0 | 5 | 764 ± 103 | ± | 8 I* | 13 I |
| M.butyricum (FCA) | 50 | 5 | 2968 ± 369.40 | 4 to 5+ | 14 I | 17/5** |
| N.rubra Cy I | 100 | 5 | 3400 ± 268 | 4 to 5+ | 14 I | 15/3 |
| N.rubra Cy II | 100 | 5 | 3876 ± 658 | 5+ | 10 I | 12 I |
| N.rubra Cy III | 100 | 5 | 2734 ± 685 | 3 to 4+ | 8 I | 13/2 |
| N.rubra "lyophilized cytoplasmic crude fraction" | 100 | 5 | 2728 ± 651 | 3 to 4+ | 12 I | 18 I |
| N.opaca Cy I | 100 | 5 | 2792 ± 686 | 3 to 4+ | 12 I | 16/4 |

*I = induration
**the first number is the diametre of the erythema, the second one is the diametre (mm) of the necrosis The biological effects of the agents according to the invention make them suitable for various applications, of which some are indicated hereafter by way of examples:

(a) biological reagent for research of great interest which permits the stimulation of the B lymphocytes in several animal species, the monkey and even man;

(b) medical biological reagent, for diagnosis, from the cells of the lymph organ cells, of immunity deficiencies relating to the cells which produce antibodies;

(c) preventive treatment: after the injection of the product (preferably chosen from among the water-soluble agents) in the animal, a global and non-specific stimulation is observed which produces an increase of the antibodies directed against large categories of antigens;

(d) use, above all of the water-soluble mitogenic agents, in the curative treatment of the deficiency diseases of the bone marrow having accidental causes (for example irradiation) or idiopathic causes (for example myelo-sclerosis) and for the stimulation of stem cells. They are then administered preferably by injection in association with injectable sterile liquid vehicles, such as a saline or glucose isotonic solution.

The hydrosoluble mitogenic agents are valuable, particularly in that it is possible to use them in the form of oil-free compositions.

We claim:

1. A method for obtaining a water-soluble agent having mitogenic and/or adjuvant properties in-vivo and in-vitro comprising the steps of:
   rupturing by physical pressure non-delipidated whole cells of Nocardia within an aqueous medium, forming an aqueous phase and a solid phase comprising cells including ruptured cells, and separating the solid phase and recovering the aqueous phase, which phase is virtually free of cell wall constituents also of the peptidoglycan constituents, but having constituents of the cell cytoplasm, the aqueous phase having adjuvant and/or mitogenic properties.

2. The method of claim 1, further comprising separating a second solid phase comprising cytoplasmic constituents and ribosomes, and a second aqueous phase having mitogenic and/or adjuvant properties.

3. The method of claim 2, further comprising separating said second aqueous phase essentially free of cytoplasmic constituents and ribosomes into a third solid phase and a third liquid phase comprising non-centrifugable cytosols and having mitogenic and/or adjuvant properties, the third solid phase having ribosomes and mitogenic and/or adjuvant properties and being free of cytosols.

4. The method of claim 1, wherein the separating step is carried out by centrifugation.

5. The method of claim 2, wherein the separating step is carried out by centrifugation.

6. The method of claim 3, wherein the separating step is carried out by ultra-centrifugation.

7. The method of claim 6, wherein said ultra-centrifugation is at least 100,000 g.

8. The method of claim 6, wherein prior to said ultra-centrifugation, there is added to said second liquid phase containing residual ribosomes, a precipitation agent which promotes the precipitation of the ribosomes.

9. The method of claim 8, wherein the precipitation agent is magnesium chloride.

10. The method of claim 4, wherein said centrifugation is at about 27,400 g.

11. The method of claim 1, wherein the rupturing step is by physical grinding means.

12. The method of claim 5, wherein said centrifugation is at about 48,000 g.

13. The method of claim 1, wherein after said rupturing step and prior to said forming of an aqueous phase and a solid phase, the aqueous composition is subjected to a separation whereby a deposit of unbroken cells is formed and discarded and the aqueous phase produced which contains the insoluble ruptured cells is subjected to said forming step.

14. The method of claim 13, whereby said separation is by centrifugation.

15. The method of claim 1, wherein said cells of Nocardia are cells of *Nocardia rubra* or *Nocardia opaca*.

16. The method of claim 15, wherein said cells are cells of *Nocardia rubra*.

17. The method of claim 15, wherein said cells are cells of *Nocardia opaca*.

18. The method of claim 1, further comprising the step of lyophilizing said aqueous phase.

19. The method of claim 2, wherein said cells are cells of *Nocardia rubra* and said second solid phase is mitogenic.

20. The method of claim 18, wherein said cells are cells of *Nocardia rubra*.

21. The method of claim 1, wherein the rupturing of the whole cells is by pressure grinding.

22. The method of claim 1, wherein the rupturing of the whole cells is by homogenizing within an aqueous medium.

23. A pharmaceutical composition which comprises a pharmaceutically acceptable carrier and a water-soluble cytoplasmic extract from non-delipidated Norcardia peptidoglycan containing cells which has mitogenic and/or adjuvant properties.

24. The pharmaceutical composition of claim 23 wherein the carrier is an aqueous isotonic sterile injectable solution.

25. The pharmaceutical composition of claim 23 wherein the carrier is oil-free.

26. The pharmacetical composition of claim 23, wherein said cells of Nocardia are cells of *Nocardia rubra* or *Nocardia opaca*.

27. The pharmaceutical composition of claim 26, wherein said cells are cells of *Nocardia rubra*.

28. The pharmaceutical composition of claim 26, wherein said cells are cells of *Nocardia opaca*.

29. The pharmaceutical composition of claim 23, wherein said extract is free of cell wall constituents and peptidoglycans.

30. The pharmaceutical composition of claim 29, wherein said extract has been subjected to lyophilization.

31. The pharmaceutical composition of claim 23, wherein said extract comprises cytoplasmic membrane and ribosomes.

32. The pharmaceutical composition of claim 31, wherein said cells are cells of *Nocardia rubra* and said composition is mitogenic at doses of 100 $\mu$g per kg of the host.

33. The pharmaceutical composition of claim 23, wherein said composition is mitogenic at a dose of 100 $\mu$g of agent per kg of the host.

34. The pharmacetical composition of claim 23, wherein said composition is an adjuvant at a dose of 100 mg of agent per kg of the host.

35. The pharmaceutical composition of claim 23, wherein said extract is free of cytosols.

36. A pharmaceutical composition comprising a pharmaceutically acceptable carrier and a mitogenic water-soluble cytoplasmic agent from non-delipidated *Nocardia rubra* cells comprising cytoplasmic membrane and ribosomes, said agent being free of cell wall constituents and peptidoglycan constituents.

* * * * *